(12) United States Patent
Chu

(10) Patent No.: US 7,122,039 B2
(45) Date of Patent: Oct. 17, 2006

(54) TYING KNOTS

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 534 days.

(21) Appl. No.: 10/136,256

(22) Filed: May 1, 2002

(65) Prior Publication Data

US 2003/0208208 A1 Nov. 6, 2003

(51) Int. Cl.
*A61B 17/04* (2006.01)
(52) U.S. Cl. ...................... 606/144; 606/148
(58) Field of Classification Search ............... 606/139, 606/144, 145, 148, 103; 289/17; 439/207; 600/233
See application file for complete search history.

(56) References Cited

U.S. PATENT DOCUMENTS

| | | | | |
|---|---|---|---|---|
| 2,689,147 | A | * 9/1954 | Smalley | 289/17 |
| 3,840,017 | A | 10/1974 | Violante | 128/340 |
| 4,274,398 | A | * 6/1981 | Scott, Jr. | 600/233 |
| 4,434,791 | A | * 3/1984 | Darnell | 600/233 |
| 4,553,543 | A | * 11/1985 | Amarasinghe | 606/148 |
| 4,602,635 | A | 7/1986 | Mulhollan et al. | |
| 4,617,933 | A | * 10/1986 | Hasson | 606/148 |
| 4,702,250 | A | * 10/1987 | Ovil et al. | 606/148 |
| 4,957,498 | A | 9/1990 | Caspari et al. | 606/146 |
| 5,087,263 | A | 2/1992 | Li | |
| 5,176,691 | A | 1/1993 | Pierce | |
| 5,183,971 | A | * 2/1993 | Lafosse et al. | 439/207 |
| 5,324,298 | A | 6/1994 | Phillips et al. | |
| 5,336,230 | A | 8/1994 | Leichtling et al. | |
| 5,364,408 | A | 11/1994 | Gordon | |
| 5,364,409 | A | 11/1994 | Kuwabara et al. | |
| 5,391,176 | A | 2/1995 | de la Torre | |
| 5,439,467 | A | 8/1995 | Benderev et al. | |
| 5,454,820 | A | 10/1995 | Kammerer et al. | |
| 5,458,609 | A | 10/1995 | Gordon et al. | |
| 5,527,323 | A | 6/1996 | Jervis et al. | |
| 5,536,273 | A | 7/1996 | Lehrer | |
| 5,540,704 | A | 7/1996 | Gordon et al. | |
| 5,562,684 | A | 10/1996 | Kammerer | |
| 5,578,044 | A | 11/1996 | Gordon et al. | |
| 5,591,179 | A | 1/1997 | Edelstein | 606/144 |
| 5,609,597 | A | 3/1997 | Lehrer | |

(Continued)

FOREIGN PATENT DOCUMENTS

WO WO 96/27331 9/1996

OTHER PUBLICATIONS

LSI Solutions, "The Device to Instantly Secure and Trim Suture" 5mm Titanium Knot Placement Device, www.lsisolutions.com, pp. 21.

*Primary Examiner*—Julian W. Woo
(74) *Attorney, Agent, or Firm*—Edwards Angell Palmer & Dodge LLP

(57) ABSTRACT

A suture knot can be tied during a medical procedure by use of a suture retainer ring in connection with a suturing instrument. The retainer ring allows a user to orient a suture about the instrument, such that a knot in the suture is automatically advanced and tightened by withdrawing the instrument from a surgical site after placing the suture. The retainer ring can be an integral part of the suturing instrument, or it can be removably coupled to the suturing instrument to facilitate use of the retainer ring with other suturing instruments.

10 Claims, 15 Drawing Sheets

U.S. PATENT DOCUMENTS

| | | |
|---|---|---|
| 5,643,293 A | 7/1997 | Kogasaka et al. |
| 5,653,719 A | 8/1997 | Raiken |
| 5,662,663 A | 9/1997 | Shallman ..................... 606/144 |
| 5,681,331 A | 10/1997 | de la Torre et al. |
| 5,713,910 A | 2/1998 | Gordon et al. |
| 5,716,368 A | 2/1998 | de la Torre et al. |
| 5,716,369 A | 2/1998 | Riza |
| 5,741,277 A | 4/1998 | Gordon et al. |
| 5,746,752 A | 5/1998 | Burkhart |
| 5,769,862 A | 6/1998 | Kammerer et al. |
| 5,797,928 A | 8/1998 | Kogasaka |
| 5,797,929 A | 8/1998 | Andreas et al. |
| 5,860,992 A | 1/1999 | Daniel et al. |
| 5,871,489 A * | 2/1999 | Ovil ........................... 606/148 |
| 5,873,876 A | 2/1999 | Christy |
| 5,897,564 A | 4/1999 | Schulze et al. |
| 5,902,312 A | 5/1999 | Frater et al. |
| 5,908,428 A | 6/1999 | Scirica et al. ................ 606/139 |
| 5,919,199 A | 7/1999 | Mers Kelly et al. ......... 606/139 |
| 5,931,844 A | 8/1999 | Thompson et al. |
| 5,944,739 A | 8/1999 | Zlock et al. |
| 5,968,056 A | 10/1999 | Chu et al. |
| 6,048,351 A | 4/2000 | Gordon et al. |
| 6,203,554 B1 | 3/2001 | Roberts |
| 6,346,111 B1 | 2/2002 | Gordon et al. |
| 6,468,207 B1 * | 10/2002 | Fowler, Jr. ................... 600/233 |
| 6,817,634 B1 * | 11/2004 | Champion ................... 289/17 |

\* cited by examiner

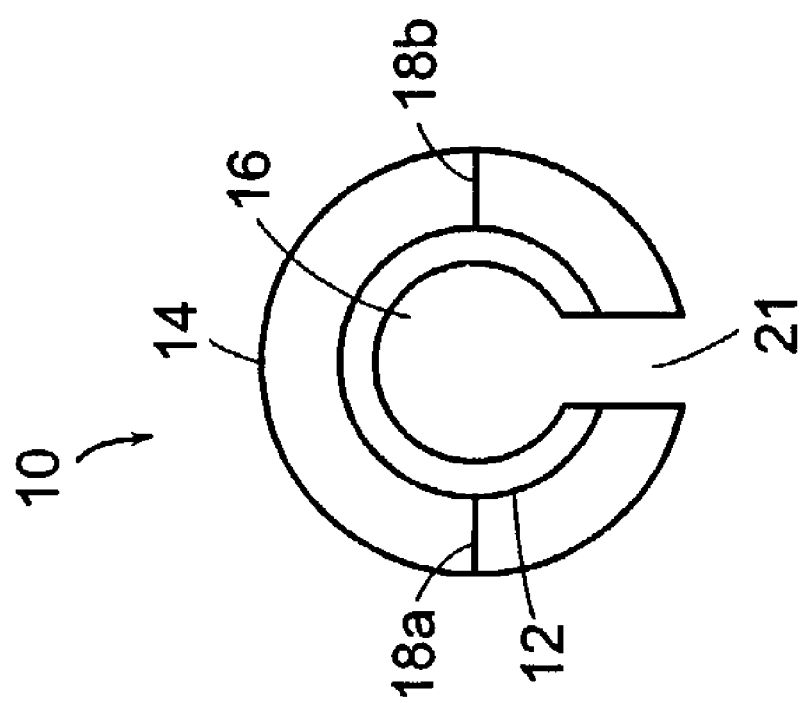

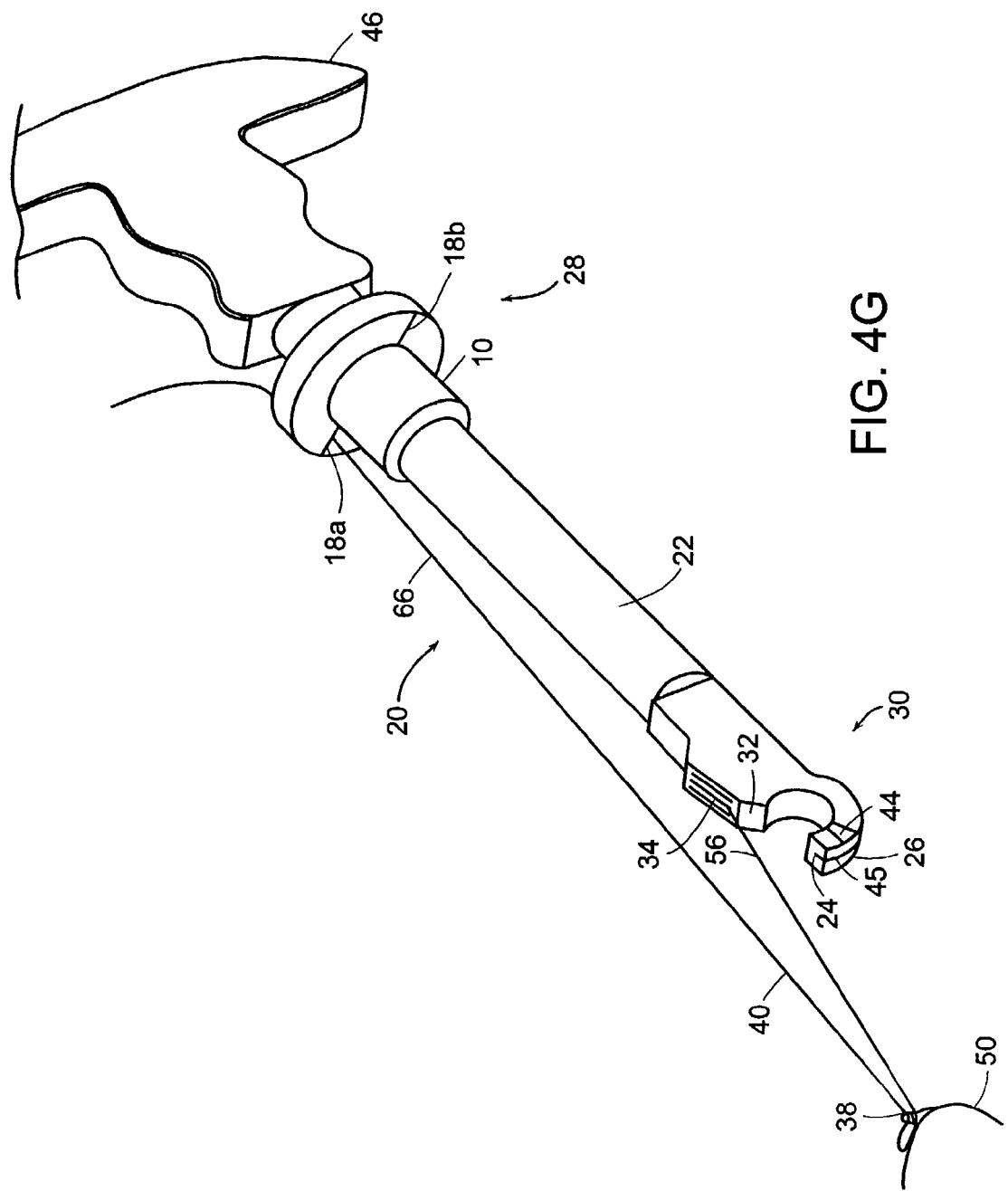

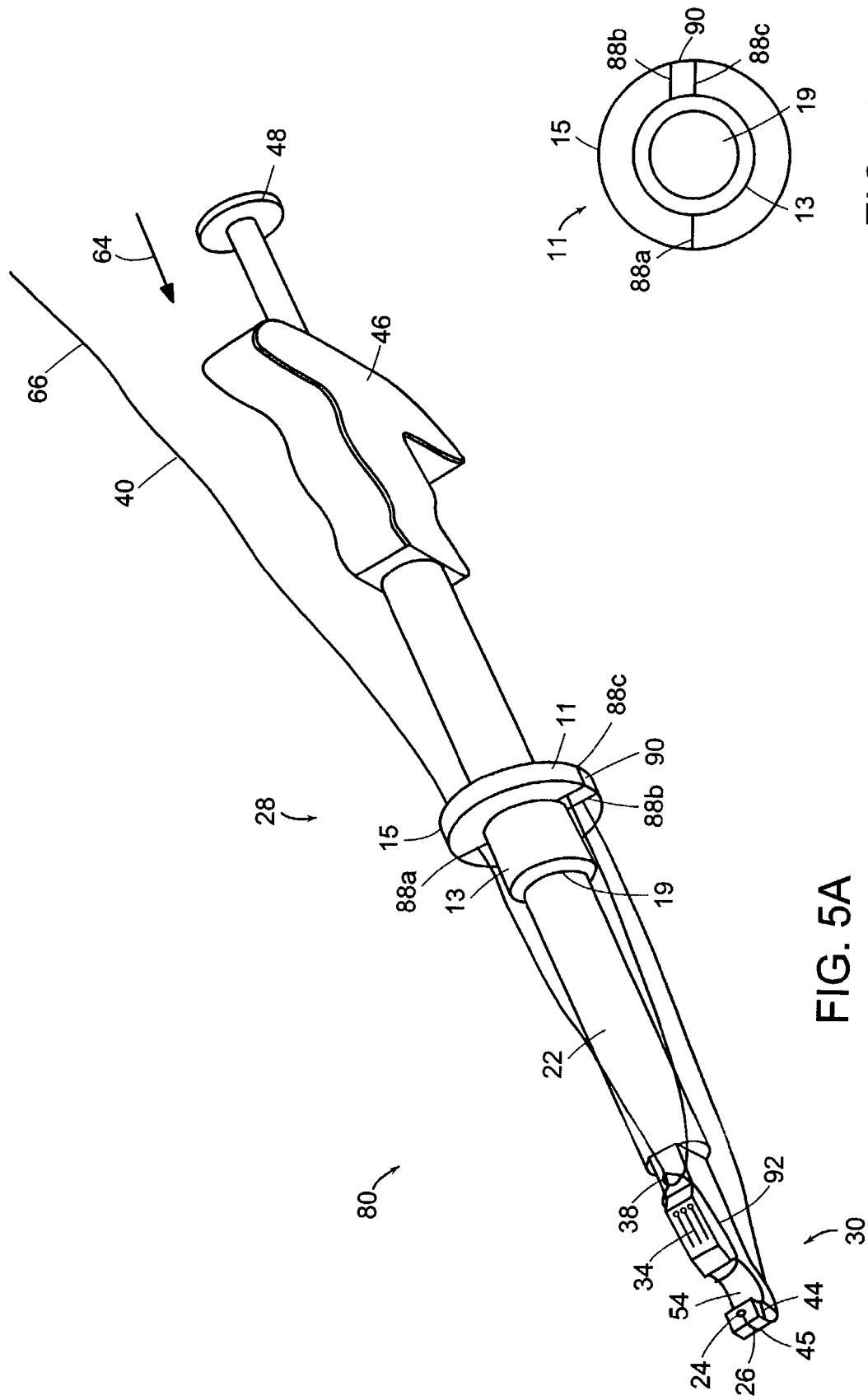

TYING KNOTS

TECHNICAL FIELD

The invention relates to devices and methods for tying knots.

BACKGROUND INFORMATION

Suturing of body tissue is a time consuming aspect of many surgical procedures. For many surgical procedures, it is necessary to make a large opening in the human body to expose the area that requires surgical repair. There are instruments available that allow for viewing of certain areas of the human body through a small puncture wound without exposing the entire body cavity. These instruments, called endoscopes, can be used in conjunction with specialized surgical instruments to detect, diagnose, and repair areas of the body that previously required open surgery to access.

Some surgical instruments used in endoscopic procedures are limited by the manner in which they access the areas of the human body in need of repair. In particular, the instruments may not be able to access tissue or organs located deep within the body or that are in some way obstructed. Also, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

Another difficult and time-consuming aspect of suturing tissue is tying the suture into a knot. The type and placement of the knot will depend on the nature of the surgical procedure, for example, ligation, fixation, or approximation; however, regardless of the type of procedure, it is necessary to manipulate the ends of the suture to form the required loop(s) to tie the knot. Further, it is subsequently necessary to manipulate and position the knot relative to the tissue. The manipulation and positioning of the suture and knot is difficult, because there may be limited space in which to work and limited visual access to the final position of the knot, in particular in an endosurgical environment.

SUMMARY OF THE INVENTION

The invention generally relates to devices and methods for simplifying the tying of knots during a medical procedure. Suture knots can be tied by use of a suture retainer ring in connection with a suturing instrument. The retainer ring allows a user to orient a suture about the instrument, such that a suture knot is automatically advanced and tightened by withdrawing the instrument from a surgical site after placing the suture. The retainer ring can be an integral part of the suturing instrument, or it can be removably coupled to the suturing instrument to facilitate use of the retainer ring with other suturing instruments.

In one aspect, the invention is directed to a suturing instrument. The instrument includes an elongate body member and a collar. The elongate body member has a distal portion. The distal portion of the elongate body member defines an opening. The collar is disposed about the elongate body member and defines two slits. In some embodiments, the collar includes a body that defines an opening therethrough. The collar can further include a protrusion disposed on the body. The body can be cylindrical and the protrusion can be a ring circumferentially disposed about the body. The ring can include a flexible material, and the slits can be radially disposed on a circumference of the ring. In addition, the slits can extend substantially the entire length of the ring.

In other embodiments, the distal portion of the elongate body member can also define a slot in communication with the opening in the distal portion of the elongate body member. Further, a needle catch can be disposed on the distal portion of the elongate body member. In various embodiments, the collar comprises a flexible material and the two slits are disposed proximate one another to form a flexible flap. In one embodiment, the two slits can be disposed about 180 degrees apart. In another embodiment, the collar can define a third slit. The third slit can be disposed proximate one of the two slits. Further, the collar can be slidably disposed on the elongate body member.

In another aspect, the invention relates to a suture retaining device. The device includes a body having an opening therethrough and a protrusion disposed on the body. The protrusion defines two slits.

In various embodiments, the body can be cylindrical and the protrusion can be a ring circumferentially disposed about the body with the slits being disposed on a circumference of the ring. The ring can be circumferentially disposed about a midline of the body. The slits can be radially disposed on a circumference of the ring. The protrusion can include a flexible material with the two slits radially disposed and proximate one another to form a flexible flap. In one embodiment, the ring can include a third slit disposed on the circumference of the collar. The third slit can be radially disposed proximate one of the two slits. In another embodiment, the two slits can be disposed about 180 degrees apart. Further, the body can be slidably disposed on a suturing instrument.

In another aspect, the invention relates to a method of tying a knot with a suturing instrument. The method includes the steps of inserting a needle and a suture attached thereto into an opening defined by a distal portion of the suturing instrument, lacing the suture through a slot defined by the distal portion and disposed adjacent the opening on the suturing instrument, forming a first loop with the suture, inserting the first loop into a slit defined by a collar disposed on a proximal portion of the suturing instrument, forming a second loop by wrapping the suture about a protuberance disposed on the distal portion of the suturing instrument and threading the suture through the second loop, and inserting the suture into a second slit defined by the collar. In one embodiment, the method also includes the steps of inserting the suturing instrument within an opening in a body, advancing the needle through tissue in the body and into a needle catch, and withdrawing the suturing instrument from the body thereby pulling the first loop from the first radial slit and releasing the second loop from about the needle catch.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 3D is a schematic end view of an alternative embodiment of a suture retaining device in accordance with the invention;

FIGS. 4A–4H are schematic perspective views of the suturing instrument of FIG. 1 in use;

FIG. 5A is a schematic perspective view of an alternative suturing instrument in accordance with the invention; and FIG. 5B is a schematic end view of the suture retaining device of FIG. 5A.

DESCRIPTION

In general, the invention relates to improvements in suturing devices, such as those disclosed in U.S. Pat. Nos. 5,364,408 and 6,043,851, each of which is incorporated by reference herein in its entirety. Further, the invention generally relates to devices and methods for simplifying the tying of suture knots during a medical procedure. A device according to the invention can be used intracorporally to facilitate the tying of suture knots by incorporating a suture retainer ring onto a suturing instrument. The suture retainer ring allows a user to orient the suture about the suturing instrument, such that a knot is automatically advanced and tied by withdrawing the suturing instrument from a surgical site after placing a suture. The suturing instrument can be used for sling anchoring, closing wounds, or any medical procedure where a knot is required after a suture is placed. The suturing instrument is particularly useful in medical applications where knotted sutures are required in areas of the body that are difficult to access.

Figure 1:
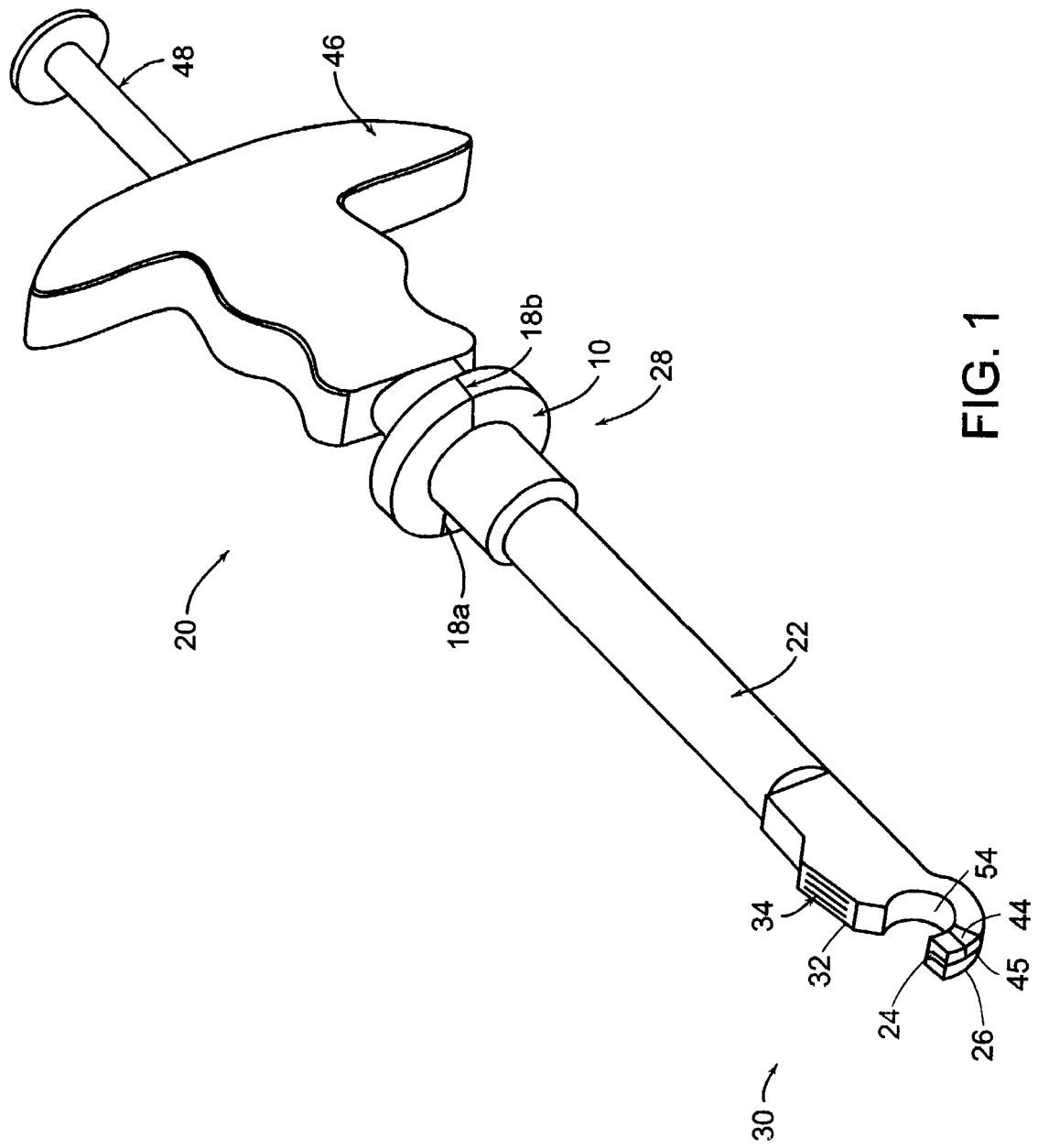
FIG. 1 is a schematic perspective view of an embodiment of a suturing instrument in accordance with the invention.

Referring to FIG. 1, in one embodiment, the suturing instrument 20 includes an elongate body member 22, a handle 46, an actuator 48, and a suture retaining device (or collar) 10 slidably disposed about a proximal portion 28 of the elongate body member 22. The proximal portion 28 of the elongate body member 22 is mechanically coupled to the handle 46. A portion of the actuator 48 is slidably disposed within the handle 46 and the elongate body member 22 and a portion of the actuator 48 extends out of the handle 46. A distal portion 30 of the elongate body member 22 includes a raised portion (or protuberance) 32 and a curved portion 44 including a knot pusher 45. The raised portion 32 includes a needle catch 34. The curved portion 44 defines a needle exit port 24 and a suture slot 26. The curved portion 44 also defines an opening 54 for receiving tissue.

Figure 2D:
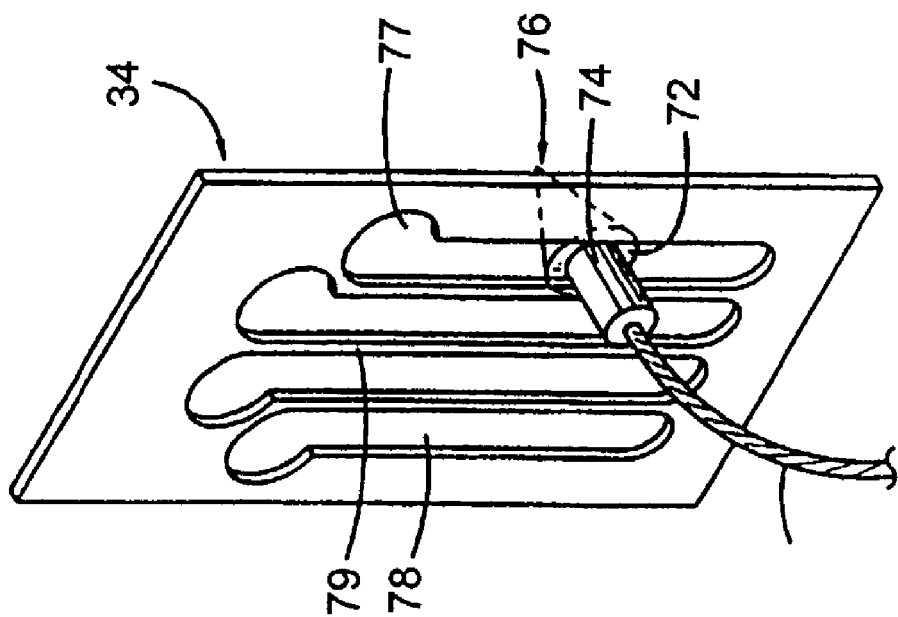
FIG. 2D is a schematic perspective view of a needle catch for use with the suturing instrument of FIG. 1.
Figure 2A:
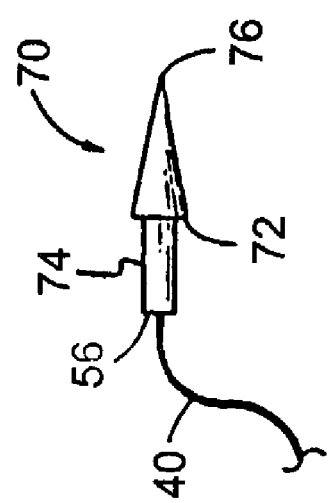
FIG. 2A is a schematic plan view of a needle coupled to a suture for use in a suturing instrument in accordance with the invention.

Referring to FIGS. 1 and 2A–2D, in one embodiment, an arcuate extendable needle holder 58 is disposed within a channel 82 in the curved portion 44. A distal portion 60 of the needle holder 58 defines a lumen 62 for holding a needle 70. In one embodiment, the needle 70 includes a tissue penetrating tip 76 and a shaft 74 coupled to the tip 76 forming a shoulder 72 (FIG. 2A). The shaft 74 is coupled to a first end 56 of a suture 40. The needle 70 is inserted into the lumen 62 and held by a slight friction fit. The suture 40 extends out of the suture slot 26.

In operation, a user pushes the actuator 48 which, in turn, pushes a spring-loaded rod 80, which pushes the needle holder 58 out of the needle exit port 24. The user continues to push the actuator 48 until the needle 70 enters the needle catch 34. The needle catch 34, as shown in FIG. 2D, includes openings 78 defined by successive ribs 79. The needle catch 34 receives the needle 70 (coupled to the suture 40) through opening 78, the ribs 79 deflect slightly to allow the needle 70 to pass through. After the formed shoulder 72 has passed the ribs 79 and the needle holder 58 has been withdrawn (by releasing the actuator 48), thereby releasing the needle 70, the ribs 79 spring back to their original position defining the openings 78. The openings 78 are chosen to be smaller in dimension than the formed shoulder 72. This causes the needle catch 34 to retain the needle 70, because, due to the flat rear surface of the shoulder 72, the needle 70 cannot pass back through the opening 78. When it is necessary to remove the needle 70 from the needle catch 34, the needle 70 may be removed via an enlarged portion 77 of the opening 78. The enlarged portion 77 is sized to allow the formed shoulder 72 to pass through without resistance. The needle catch 34 is preferably constructed of thin stainless steel of high temper, such as ANSI 301 full hard. The needle catch 34 may be fabricated by means of stamping, laser machining, or chemical etching.

Figure 3C:
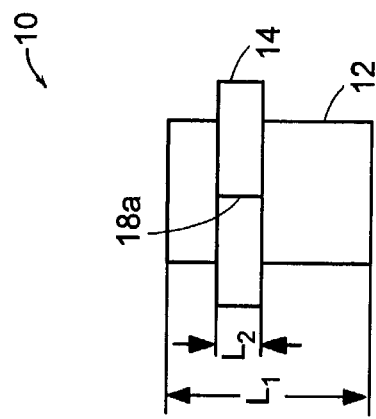
FIG. 3C is a schematic side view of the suture retaining device of FIG. 3A.
Figure 3B:
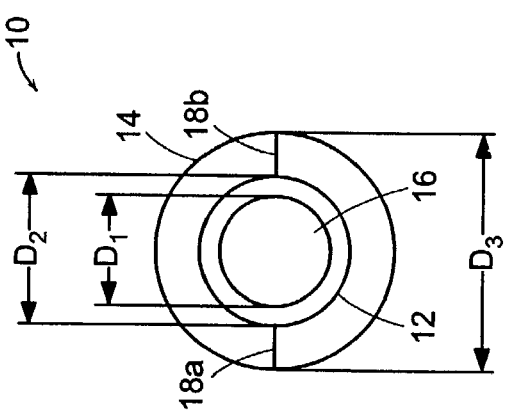
FIG. 3B is a schematic end view of the suture retaining device of FIG. 3A.
Figure 3A:
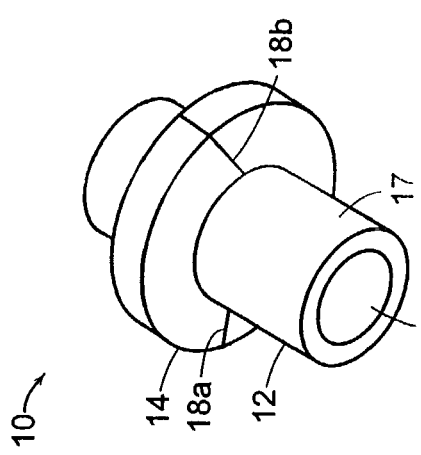
FIG. 3A is a schematic perspective view of one embodiment of a suture retaining device in accordance with the invention.

Referring to FIGS. 3A–3C, in one embodiment, the suture retaining device 10 includes a cylindrical body portion 12 that defines a body opening 16 extending therethrough. The suture retaining device 10 further includes a protrusion 14 coupled to an outer surface 17 of the body portion 12. In the embodiment shown, the protrusion 14 is a ring circumferentially disposed about the body 12. The ring 14 is coaxial with the body portion 12 and defines a first slit 18a and a second slit 18b. The slits 18a, 18b are radially disposed approximately 180 degrees apart on the ring 14 and extend through the length $l_2$ of the ring 14 in a direction parallel to the axis of the body portion 12 and the ring 14. Alternatively, the slits 18a, 18b could extend non-radially and/or not extend completely through the ring 14. The elongate body member 22 (FIG. 1) extends through the body opening 16, such that the suture retaining device 10 is manually slidable along the elongate body member 22. The position of the suture retaining device 10 along the elongate body member 22 is maintained through a friction fit. In an alternative embodiment (FIG. 3D), the body portion 12 and the ring 14 can define a gap 21. The gap 21 can be enlarged to allow the suture retaining device 10 to be clipped onto the elongate body member 22.

In various embodiments of the suture retaining device 10, the inside diameter $D_1$ of the body portion 12 is about 0.15 to 0.60 inches and preferably about 0.4 inches, the outside diameter $D_2$ of the body portion 12 is about 0.25 to 0.75 inches and preferably about 0.5 inches, and the outside diameter $D_3$ of the ring 14 is about 0.75 to 1.5 inches and preferably about 1.1 inches. The length $l_1$ of the body portion 12 is about 0.5 to 1.0 inches and preferably about 0.7 inches, and the length $l_2$ of the ring 14 is about 0.06 to 0.18 inches and preferably about 0.13 inches. In alternative embodiments, the body portion 12 can be of a shape other than cylindrical, such as elliptical or rectangular, for example. The shape and material chosen for the suture retaining device 10 will vary to suit a particular application. In still other embodiments, the ring 14 can be replaced by one or more than one protrusion(s) disposed on the body portion 12.

The suturing instrument's component materials should be biocompatible. For example, the handle 46, the elongate body member 22, the suture retaining device 10, and portions of the actuator 48 may be fabricated from extruded, molded, or machined plastic material(s), such as polypropylene, polycarbonate, glass-filled polycarbonate, or other medical grade plastic. Other components, for example the needle 70, may be made of stainless steel. Other suitable materials will be apparent to those skilled in the art. The type of material(s) used to form the suture 40 is not critical to the present invention, as long as the material is biocompatible. The surgeon will select the length, diameter, and characteristics of the suture to suit a particular application.

Figure 2B:
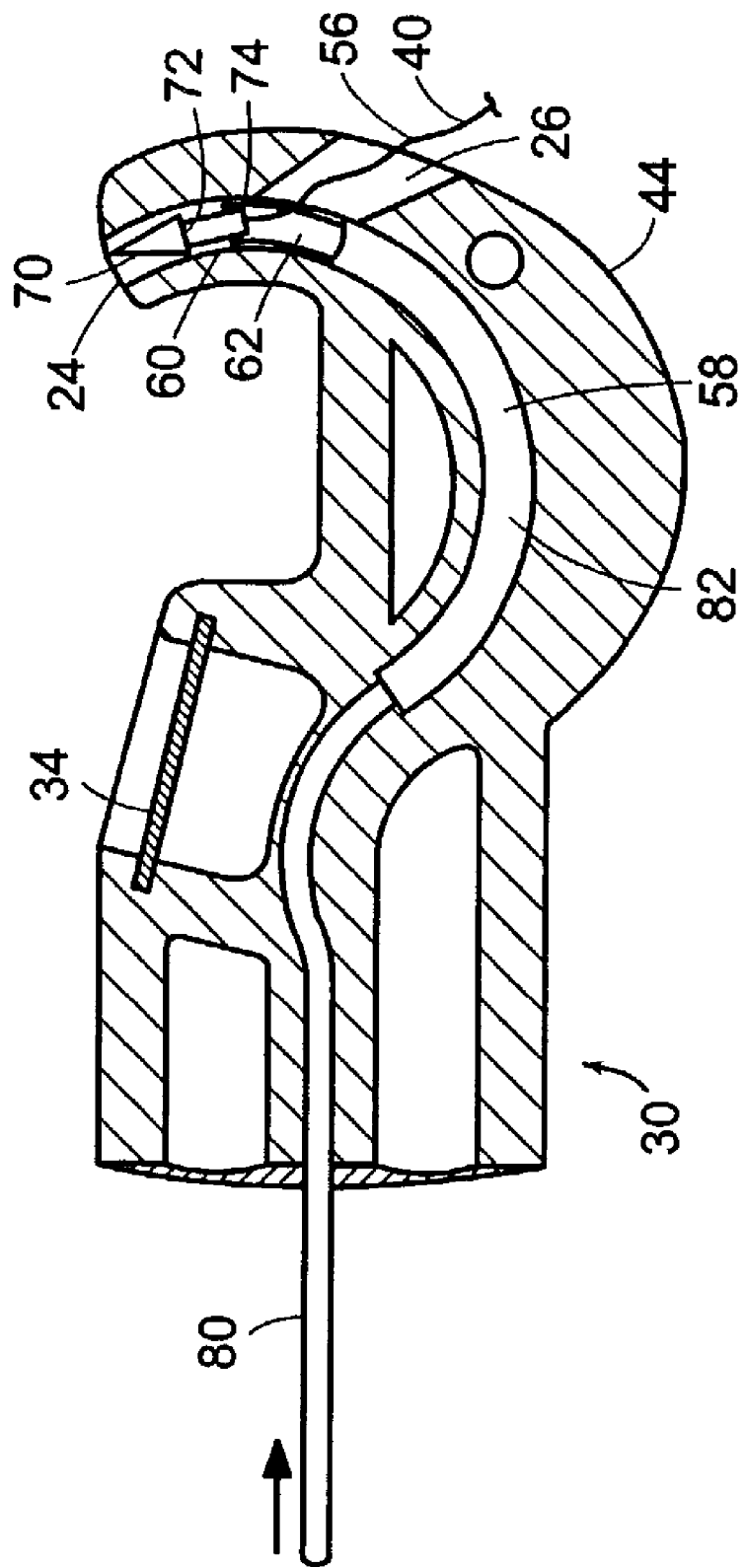
FIG. 2B is a schematic cross-sectional view of a distal portion of the suturing instrument of FIG. 1 with the needle in a retracted position.
Figure 2C:
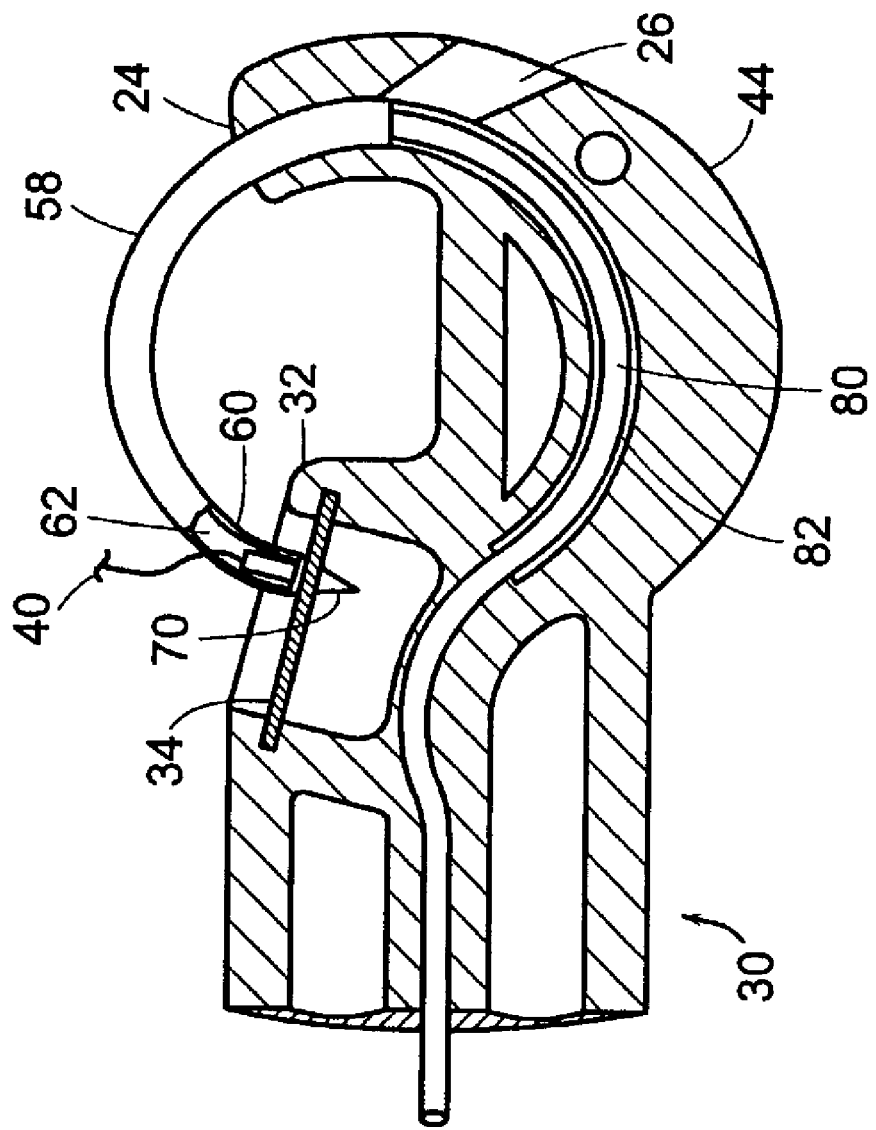
FIG. 2C is a schematic cross-sectional view of the distal portion of the suturing instrument of FIG. 1 with the needle in an advanced position.
Figure 4A:
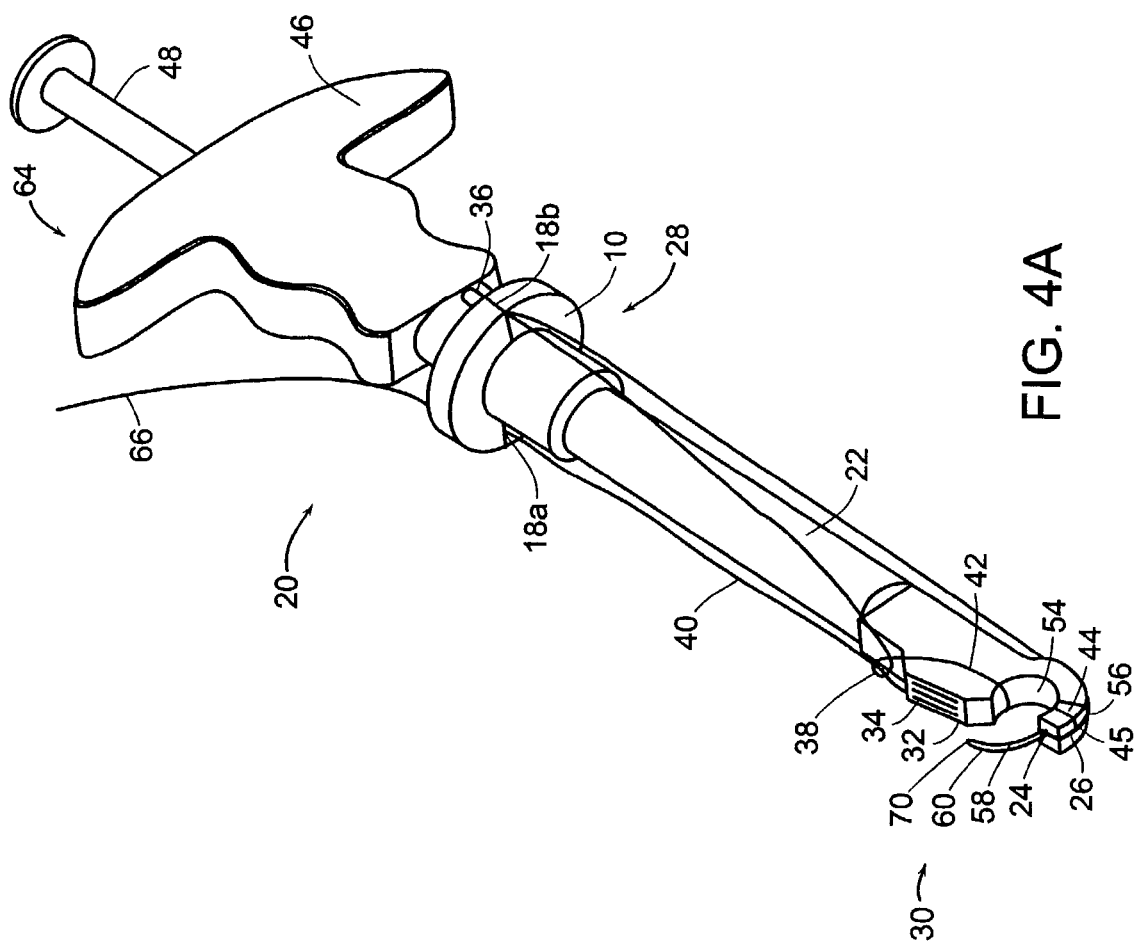

Referring to FIG. 4A, an initial configuration of the suturing instrument 20 includes loading the suturing instrument 20 with a needle 70 and a suture 40. A user (e.g., physician or other medical personnel) pushes the actuator 48 in a direction indicated by arrow 64, thereby causing the needle holder 58 to extend out of the needle exit port 24. The user next inserts a needle 70 coupled to a first end 56 of the suture 40 into the lumen 62 (FIGS. 2B and 2C). After the needle 70 is loaded, the actuator 48 is released, which allows the needle holder 58 to retract into the curved portion 44. The user then runs the suture 40 through the suture slot 26 and extends the suture 40 along the elongate body member 22. The user then inserts the suture 40 into slit 18*b* and folds the suture 40 back 180 degrees and again inserts the suture 40 into slit 18*b* thereby creating a first loop 36. The user then loosely ties the suture 40 in a knot 38 forming a second loop 42. The user places the second loop 42 over the raised portion 32. The user then extends the suture 40 back along the elongate body member 22 and inserts a second end 66 into slit 18*a*. In this initial configuration, the suture 40 is slack and approximately twice as long as the length of the suturing instrument 20 that is to be inserted into a patient.

Figure 4B:
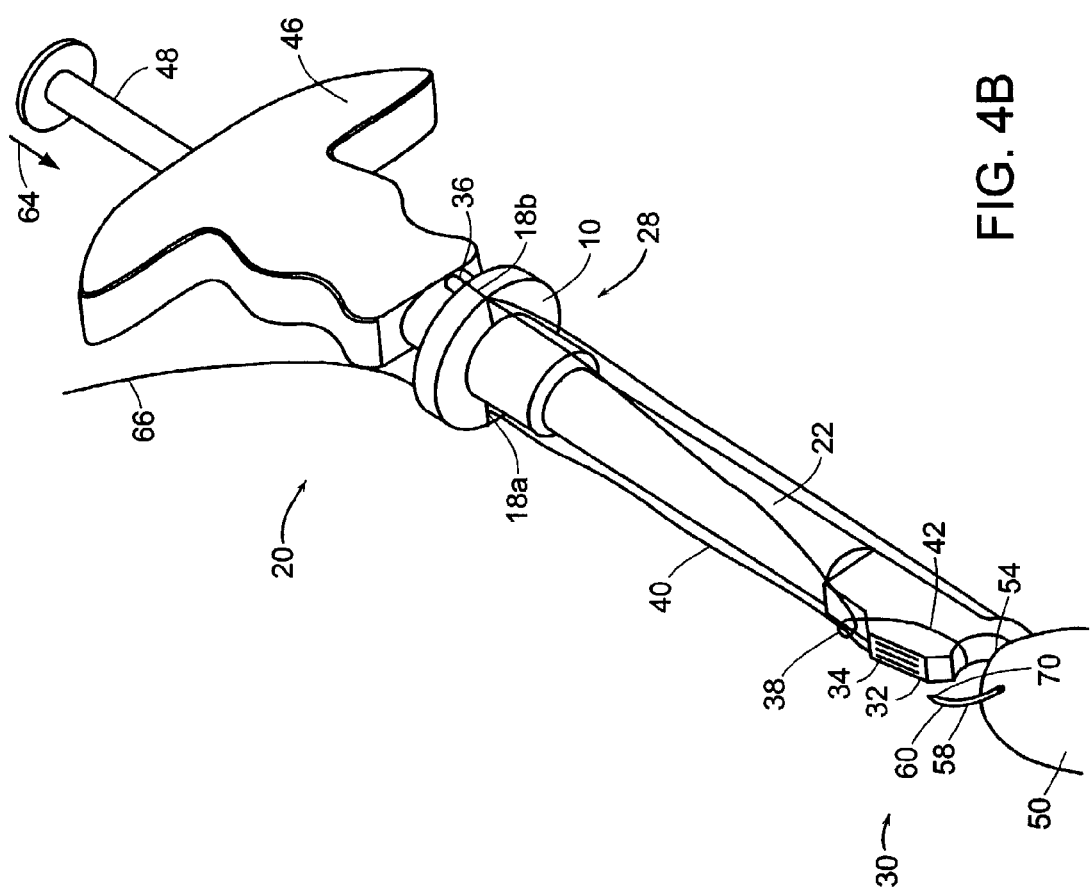
Figure 4C:
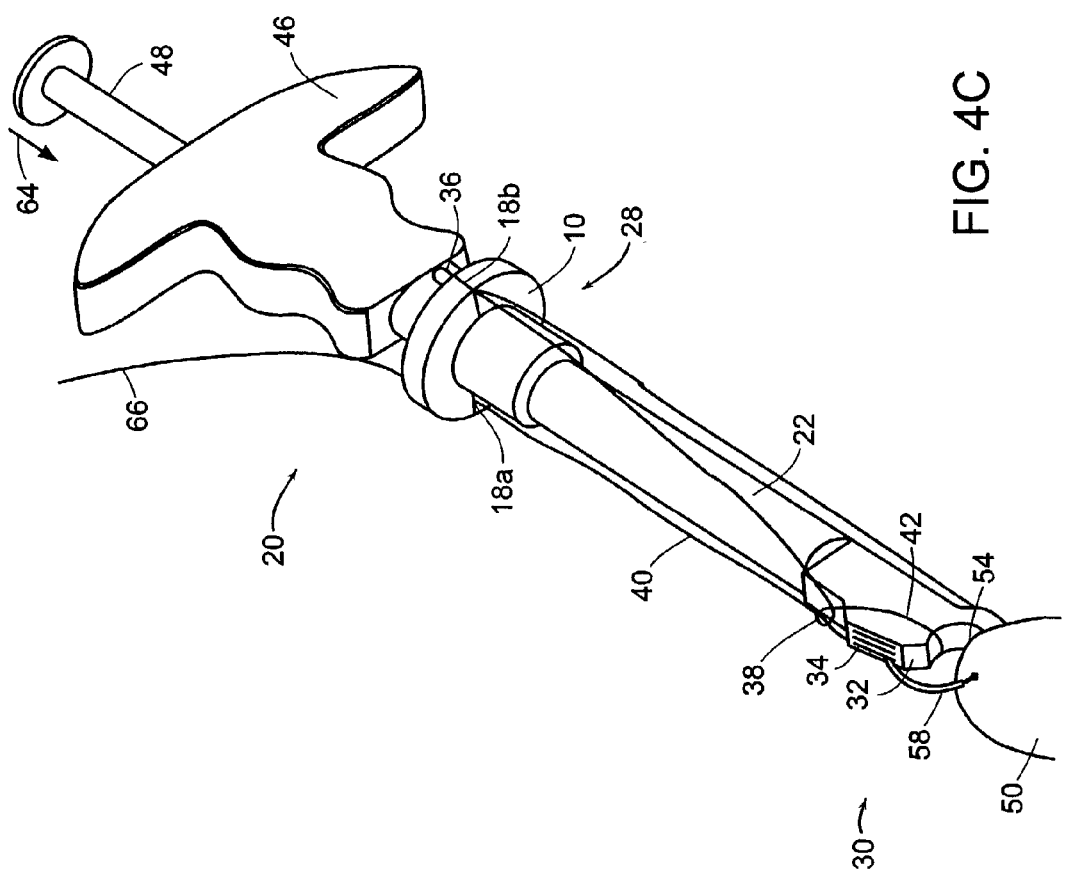

Referring to FIGS. 4A–4C, in operation, the user inserts the elongate body member 22 into a patient and orients the elongate body member 22 so that the needle exit port 24 is in contact with the tissue 50 to be sutured. The user then pushes the actuator 48 in the direction indicated by arrow 64. Pushing the actuator causes the needle holder 58 (holding the needle 70) to extend out of the needle exit port 24 and push the needle 70 through the tissue 50. As the needle 70 is pushed through the tissue 50, the needle 70 pulls the suture 40 through the tissue 50. As the user continues to push the actuator 48, the needle holder 58 continues to advance out of the needle exit port 24 and directs the needle 70 and the suture 40 toward the needle catch 34. The user continues to push the actuator 48 until the needle 70 contacts and becomes captured by the needle catch 34 (FIG. 4C).

Figure 4D:
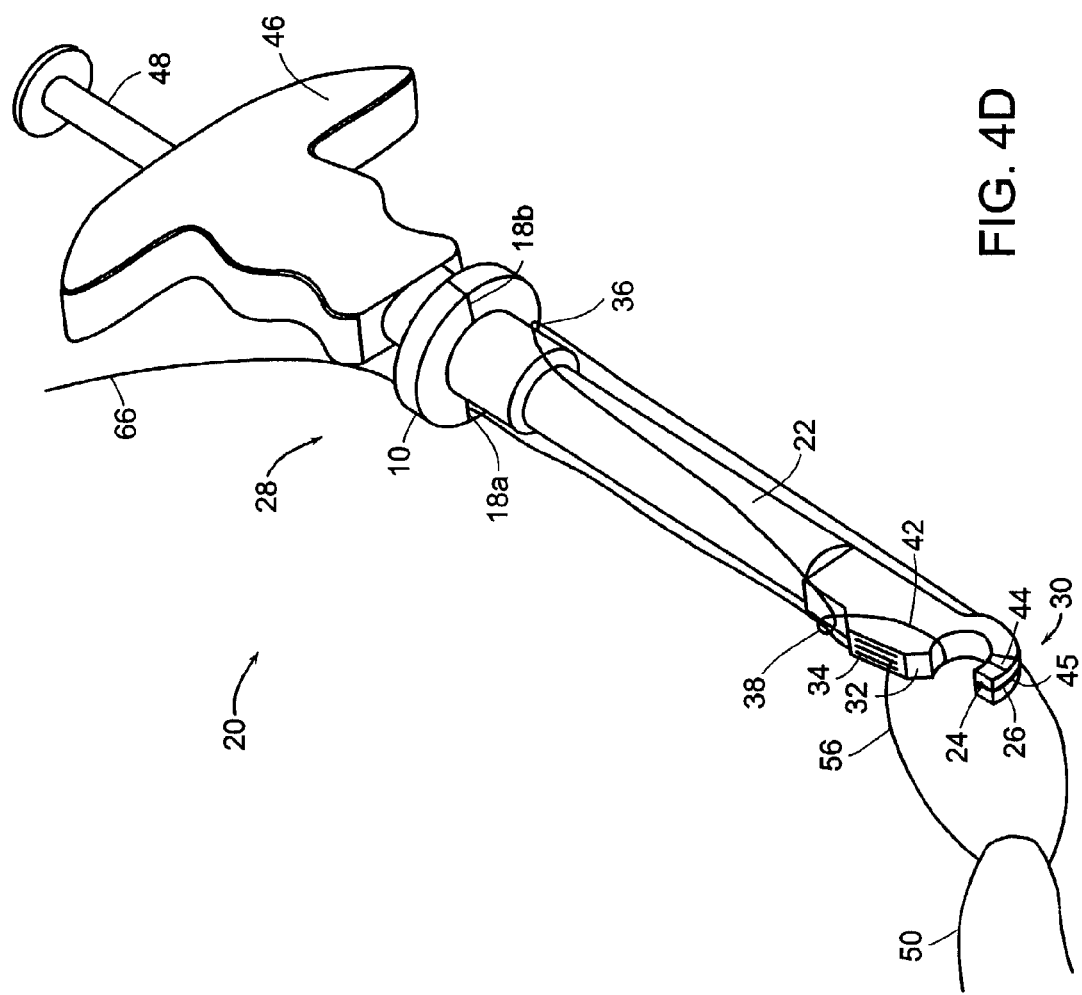
Figure 4E:
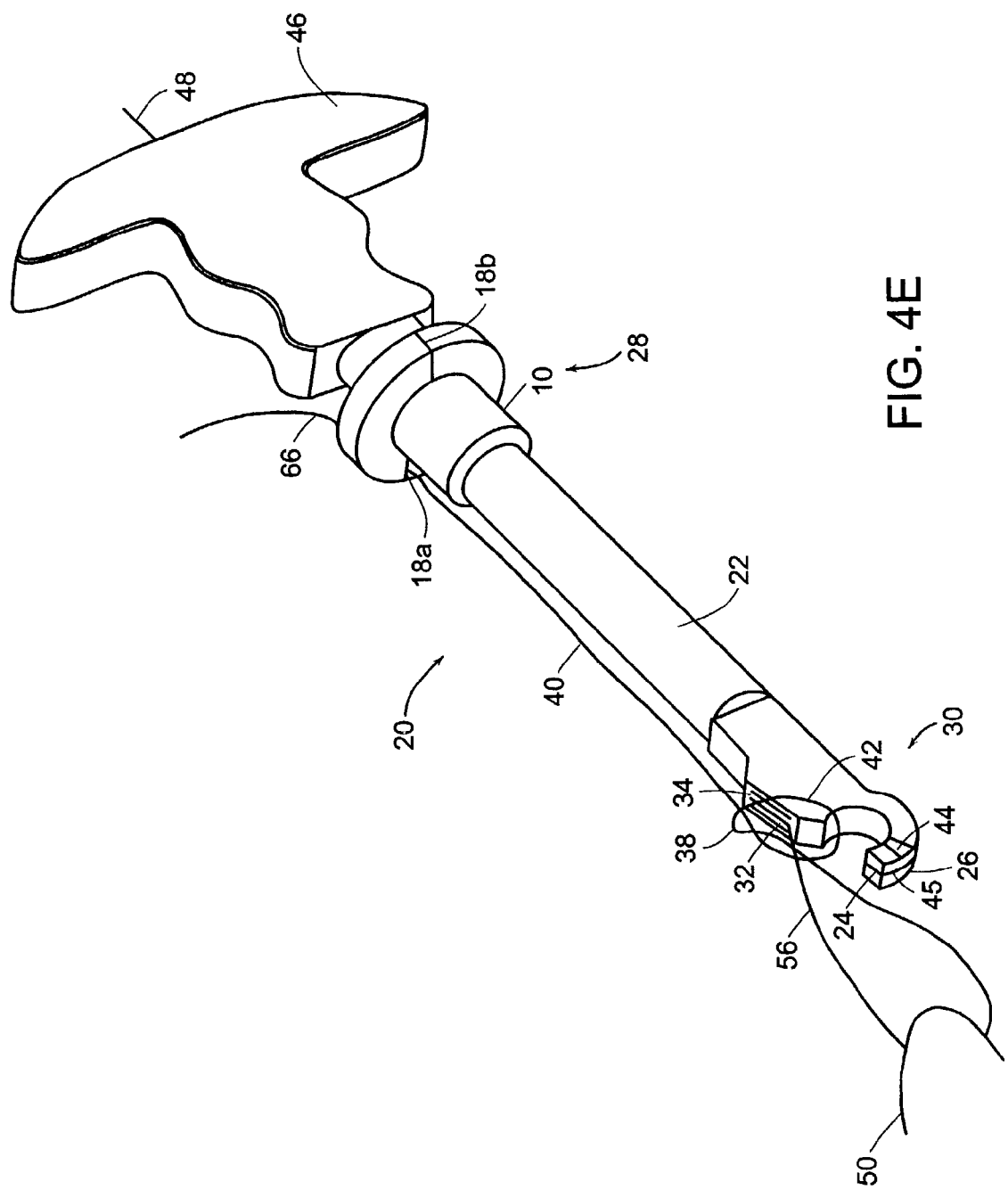
Figure 4F:
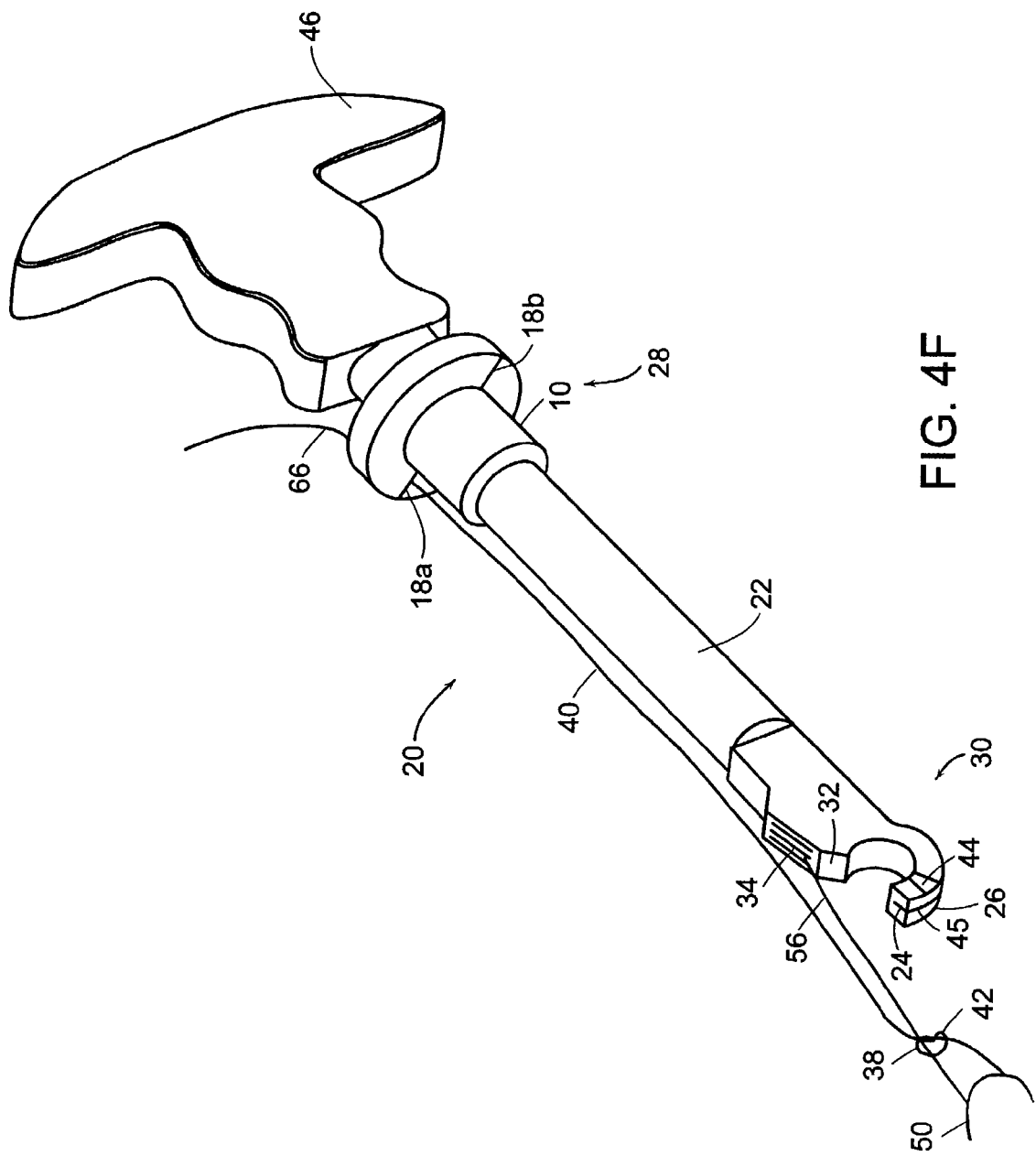

Referring to FIGS. 4D–4G, after the user retracts the needle holder 58 by releasing or pulling the actuator 48, the needle 70 and the suture 40 are left captured within the needle catch 34, with the suture 40 extending through the tissue 50. The user then pulls the suturing instrument 20 away from the tissue 50 (FIG. 4D). The first loop 36 is pulled out of slit 18*b* and the second loop 42 is subsequently pulled off the raised portion 32 and over the first end 56 of the suture 40 (FIG. 4E). As the user continues to pull the suturing instrument 20 away from the tissue 50, the first end 56 of the suture 40 is pulled through the second loop 42. The second loop 42 gradually closes and the knot 38 gradually tightens around the first end 56 of the suture 40 (FIG. 4F). Eventually, the knot 38 securely tightens around the suture 40 and is flush with the tissue 50 (FIG. 4G).

Figure 4H:
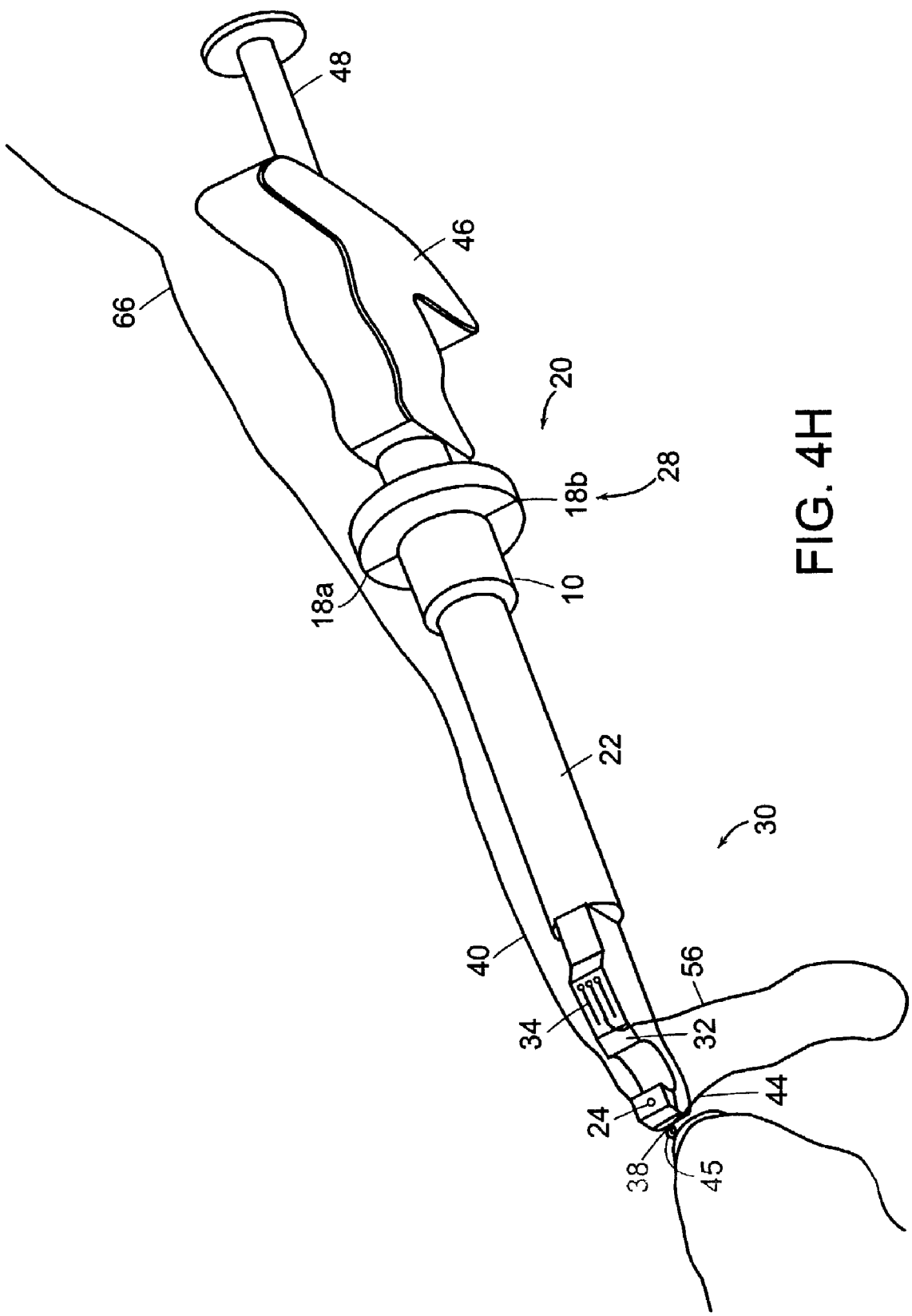

Referring to FIG. 4H, the user pushes the knot pusher 45 against the knot 38. The user then removes the second end 66 of the suture from slit 18*a* and pulls the second end 66 of the suture 40 in a direction away from the tissue 50. This optional procedure serves to further tighten the knot 38 and secure the suture 40 against the tissue 50.

In operation, the length of the suture 40 can be controlled by manually sliding the suture retaining device 10 along the elongate body member 22. For example, for a long suture 40, the user manually slides the suture retaining device 10 towards the proximal portion 28 of the elongate body member 22. For a short suture 40, the user manually slides the suture retaining device 10 towards the distal portion 30 of the elongate body member 22.

Referring to FIG. 5A, in an alternative embodiment, the suturing instrument 83 includes an elongate body member 22, a handle 46, an actuator 48, and a suture retaining device (or collar) 11 slidably disposed about the approximate midpoint of the elongated body member 22. A proximal portion 28 of the elongate body member 22 is mechanically coupled to the handle 46. A portion of the actuator 48 is slidably disposed within the handle 46 and the elongate body member 22 and a portion of the actuator 48 extends out of the handle 46. A distal portion 30 of the elongate body member 22 includes a raised portion 32 and a curved portion 44 that includes a knot pusher 45. The raised portion 32 includes a needle catch 34. The curved portion 44 defines a needle exit port 24 and a suture slot 26. The curved portion 44 also defines an opening 54 for receiving tissue.

Referring to FIG. 5B, the alternative suture retaining device 11 includes a cylindrical body portion 13 that defines a body opening 19 extending therethrough. The suture retaining device 11 further includes a ring 15 coupled to an outer surface of the body portion 13. The ring 13 is coaxial with the body portion 13 and defines a first slit 88*a*, a second slit 88*b*, and a third slit 88*c*. Slits 88*b*, 88*c* are radially disposed on the ring 13 proximate one another and about 180 degrees from radially disposed slit 88*a*. The slits 88*a*, 88*b*, 88*c* extend through the length of the ring 13 in a direction parallel to the axis of the body portion 13 and the ring 15. Alternatively, the slits 88*a*, 88*b*, 88*c* could extend non-radially and/or not extend completely through the ring 13. A flexible flap 90 separates slits 88*b* and 88*c*. The elongate body member 22 extends through the body opening 19, such that the suture retaining device 11 is slidable along the elongate body member 22. The position of the suture retaining device 11 along the elongate body member 22 is maintained through a friction fit. The materials used to make this alternative embodiment are similar to those previously described.

Referring again to FIG. 5A, an initial configuration of the suturing instrument 83 includes loading the suturing instrument 83 with a needle 70 and a suture 40. A user pushes the actuator 48 in a direction indicated by arrow 64, thereby causing the needle holder 58 to extend out of the needle exit port 24. The user next inserts a needle 70 coupled to a first end 56 of the suture 40 into the lumen 62 (FIGS. 2B and 2C). After the needle 70 is loaded, the actuator 48 is released, which allows the needle holder 58 to retract into the curved portion 44. The user then runs the suture 40 through the suture slot 26 and extends the suture 40 along the elongate body member 22. The user then inserts the suture 40 into slit 88*b* and folds the suture 40 back 180 degrees and inserts the suture 40 into slit 88*c*. The user then loosely ties the suture 40 in a knot 38 creating a loop 92. The user places the loop 92 over the raised portion 32. The user then extends the suture 40 back along the elongate body member 22 and inserts the second end 66 into slit 88*a*. In this initial configuration, the suture 40 is slack and approximately twice as long as the length of the suturing instrument 83 that is to be inserted into the patient. The suturing instrument 83 operates largely in the same manner as the suturing instrument 20 previously described. However, instead of a loop sliding out of a single slit when the suturing instrument 83 is pulled away from the tissue 50, tension in the suture 40 causes the flexible flap 90 to bend allowing the suture 40 to slip off the flexible flap 90 and out of slits 88*b* and 88*c*.

Variations, modifications, and other implementations of what is described herein may occur to those of ordinary skill in the art without departing from the spirit and scope of the invention. Accordingly, the invention is not to be defined only by the preceding illustrative description.

What is claimed is:

1. A method of tying a knot with a suturing instrument comprising the steps of:
   inserting a needle and a suture attached thereto into an opening defined by a distal portion of the suturing instrument;
   lacing the suture through a slot defined by the distal portion and disposed adjacent the opening on the suturing instrument;
   forming a first loop with the suture;
   inserting the first loop into a slit defined by a collar disposed on a proximal portion of the suturing instrument;
   forming a second loop by wrapping the suture about a protuberance disposed on the distal portion of the suturing instrument and threading the suture through the second loop; and
   inserting the suture into a second slit defined by the collar.

2. The method of tying a knot of claim 1, further comprising the steps of:
   inserting the suturing instrument within an opening in a body;
   advancing the needle through tissue in the body and into a needle catch; and
   withdrawing the suturing instrument from the body thereby pulling the first loop from the first radial slit and releasing the second loop from about the needle catch.

3. A suturing instrument, comprising:
   an elongate body member including a distal portion that defines an opening; and
   a collar disposed about the elongate body member and defining two slits disposed proximate one another to form a flexible flap, the collar comprising:
   a body defining an opening therethrough, and
   a ring circumferentially disposed about the body, the ring comprising a flexible material, the slits being disposed on a circumference of the ring.

4. The suturing instrument of claim 3 wherein the slits are radially disposed on a circumference of the ring.

5. The suturing instrument of claim 3 wherein the body is cylindrical.

6. The suturing instrument of claim 3 wherein the slits extend substantially the entire length of the ring.

7. The suturing instrument of claim 3 further comprising a needle catch disposed on the distal portion of the elongate body member.

8. The suturing instrument of claim 3 wherein the collar further defines a third slit.

9. The suturing instrument of claim 8 wherein the third slit is disposal about 180 degrees from the two slits.

10. The suturing instrument of claim 3 wherein the collar is slidably disposed on the elongate body member.

* * * * *